(12) United States Patent
Clasen et al.

(10) Patent No.: US 8,608,472 B2
(45) Date of Patent: Dec. 17, 2013

(54) MEDICAL SUCTION APPARATUS

(76) Inventors: Stephan Clasen, Münster (DE); Martin Kayser, KÖln (DE)

( * ) Notice: Subject to any disclaimer, the term of this patent is extended or adjusted under 35 U.S.C. 154(b) by 1236 days.

(21) Appl. No.: 10/585,439

(22) PCT Filed: Jan. 7, 2005

(86) PCT No.: PCT/DE2005/000011
§ 371 (c)(1), (2), (4) Date: Aug. 6, 2009

(87) PCT Pub. No.: WO2005/065573
PCT Pub. Date: Jul. 21, 2005

(65) Prior Publication Data
US 2009/0311648 A1    Dec. 17, 2009

(30) Foreign Application Priority Data

Jan. 9, 2004   (DE) .......................... 10 2004 001 621
Nov. 5, 2004   (DE) .......................... 10 2004 054 029

(51) Int. Cl.
*A61C 17/06* (2006.01)
*A61C 1/00* (2006.01)
*A61C 3/00* (2006.01)

(52) U.S. Cl.
USPC ................................. 433/91; 433/29; 433/31

(58) Field of Classification Search
USPC ............... 433/91–96, 29–31; 606/13–18; 604/19–45; 600/241, 245, 246–248, 600/188, 189; 362/560, 573, 297, 296.09, 362/347
See application file for complete search history.

(56) References Cited

U.S. PATENT DOCUMENTS

| | | | | |
|---|---|---|---|---|
| 3,092,910 | A * | 6/1963 | Warriner | 433/31 |
| 3,777,756 | A * | 12/1973 | Lohr | 433/91 |
| 4,279,594 | A * | 7/1981 | Rigutto | 433/31 |
| 4,963,142 | A * | 10/1990 | Loertscher | 606/14 |
| 5,078,603 | A * | 1/1992 | Cohen | 433/91 |
| 5,230,622 | A * | 7/1993 | Brossoit | 433/31 |
| 5,232,362 | A * | 8/1993 | Kanas | 433/93 |
| 5,490,780 | A | 2/1996 | Riewenherm et al. | |
| 5,743,736 | A | 4/1998 | Folko et al. | |
| 5,813,856 | A * | 9/1998 | Lee | 433/31 |

(Continued)

FOREIGN PATENT DOCUMENTS

| | | |
|---|---|---|
| AU | 2003268811 A1 | 5/2004 |
| DE | 901461 C | 1/1954 |

(Continued)

OTHER PUBLICATIONS

DE 10065705 (translation of abstract only)—Jan. 24, 2002.

(Continued)

*Primary Examiner* — Yogesh Patel
(74) *Attorney, Agent, or Firm* — Cantor Colburn LLP

(57) ABSTRACT

The invention relates to a dental suction apparatus for suctioning fluids and debris from the mouth cavity of a patient during a treatment. The apparatus has a hollow base body with a longitudinal axis X-X that includes an outer surface, an inner surface, and a suction port. A mirrored surface is disposed on the inner surface of the suction port so that at least parts of the mouth cavity can be viewed through the suction port.

8 Claims, 2 Drawing Sheets

(56) References Cited

U.S. PATENT DOCUMENTS

Figure 1:
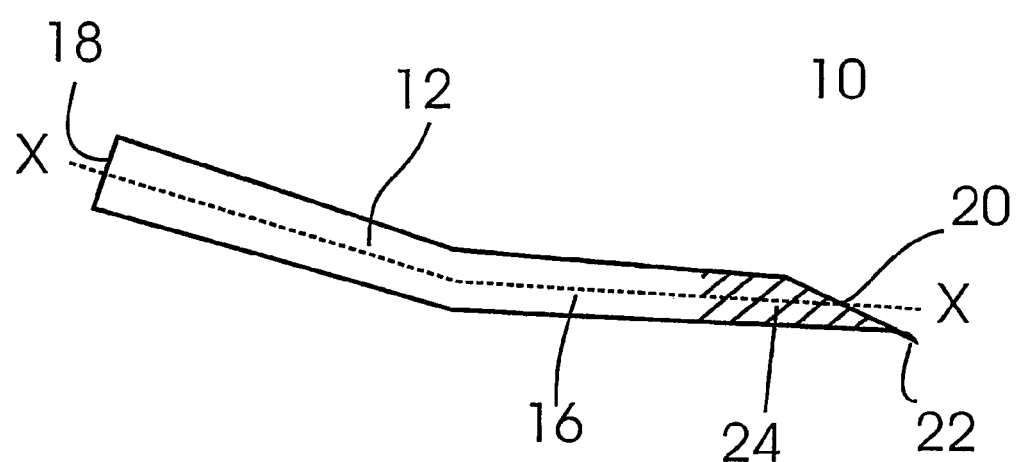

| | | | |
|---|---|---|---|
| 5,876,384 A | * | 3/1999 | Dragan et al. ................. 604/264 |
| 6,299,444 B1 | * | 10/2001 | Cohen .............................. 433/91 |
| 6,488,397 B1 | * | 12/2002 | Masutani et al. ............. 362/551 |
| 2002/0058230 A1 | * | 5/2002 | Savin et al. ..................... 433/31 |
| 2003/0124484 A1 | * | 7/2003 | Reiz ................................ 433/93 |

FOREIGN PATENT DOCUMENTS

| | | |
|---|---|---|
| DE | 901641 C | 1/1954 |
| DE | 4306450 | 3/1993 |
| DE | 10065705 A1 | 1/2002 |
| DE | 69429782 T2 | 8/2002 |
| EP | 0003470 A1 | 8/1979 |
| FR | 2595939 A1 | 9/1987 |
| WO | 94/19718 | 5/1994 |
| WO | 2004034892 A1 | 4/2004 |

OTHER PUBLICATIONS

FR 2595939 (translation of abstract only)—Sep. 25, 1987.
International Application No. PCT/DE2005/000011; International Search Report issued May 17, 2005.

* cited by examiner

MEDICAL SUCTION APPARATUS

The present invention relates to a dental suction apparatus for suctioning fluids and debris from the mouth cavity of a patient during a treatment, said apparatus having a hollow base body with a longitudinal axis X-X that comprises an outer surface, an inner surface and a suction port.

During medical and dental treatments, it is often necessary to evacuate accumulating fluids or debris from the region of treatment. During a dental treatment for example, it is necessary to suction saliva, spray water and blood during a dental visit. Also, water used for example for cleaning or for making a multifunction injection may accumulate and needs to be suctioned. The suction apparatus usually used for this purpose are generally formed from a tubular body made of plastic material at the end of which there is fastened a hose which in turn is connected to a pump. The disturbing fluids and solid matter are then suctioned through the hose or the suction apparatus.

In other medical fields as well, more specifically during surgical interventions, it is often necessary to suction blood, water and/or bone debris and similar during surgery.

Usually, a suction apparatus is not guided and held by the treating physician or surgeon but by an assistant. This is often necessary because the treating physician needs both hands for the treatment. A dentist for example often holds a drill in one hand and in the other one a mirror for viewing the region to be treated. The same applies to a surgeon who, during surgery, also often holds two instruments while still needing a mirror.

The disadvantage of the procedure described is that two persons, namely the treating physician and the assistant, must stand or sit very close together around the region to be treated in the patient. Especially if the intervention is relatively difficult or requires great fine motor skills, the treating physician often finds this disturbing.

Another disadvantage is that, if he needs to use a medical tool, a suction apparatus and a mirror, the treating physician is dependant on an assistant. This is particularly disadvantageous in dentistry, because the dental visits could often be performed without the help of an assistant but for the need for suctioning fluids or debris.

Finally, it is often disturbing that a generic suction apparatus is often in the way of the drill, meaning that working simultaneously with the drill and the suction apparatus is difficult.

It is the object of the present invention to improve a generic suction apparatus in such a manner that it is versatile on the one side and that it facilitates the treatment for the user on the other side. It is another object to make it possible for the user to perform certain tasks or treatments without the help of an assistant. The suction apparatus is thereby intended to be manufacturable at low cost and easy to utilize.

In accordance with the invention, the solution to this object is a dental suction apparatus for suctioning fluids and debris from the mouth cavity of a patient, said apparatus having a hollow base body with a longitudinal axis X-X that comprises an outer surface, an inner surface and a suction port, a mirrored surface being disposed in the region of the suction port so as to allow viewing at least parts of the mouth cavity.

Another solution to this object is a dental suction apparatus for suctioning fluids and debris from the mouth cavity of a patient during a treatment, said apparatus having a hollow base body with a longitudinal axis X-X that comprises an outer surface, an inner surface and a suction port, said base body being configured to be deformable in the longitudinal direction in such a manner that the orientation of the longitudinal axis X-X may be varied in any direction.

The reflective coating of the invention makes it possible for the user to use the medical suction apparatus both as a suction apparatus for evacuating fluids and debris and concurrently as a mirror. This is very helpful for a dentist for example who generally needs to drill and suction simultaneously when treating a tooth with a drill. Further, if he cannot view the site he wants to treat, he must use a mirror. With the help of the suction apparatus of the invention, he can now perform the treatment without the help of an assistant. Meaning, the suction apparatus is concurrently used as a mirror.

It is not necessary to provide the entire suction apparatus with a reflective coating to perform the desired function; it rather suffices to provide it in the region of the suction port. Both the inner surface and the outer surface may be coated.

Commercially commonly available suction apparatus for dental purposes generally have a suction port extending at an incline with respect to the main length of the tubular base body. Accordingly, the end of the tubular base body, which comprises the suction port, does not extend at right angles with respect to the longitudinal axis but at an incline with respect thereto. As a result, the suction apparatus has a tapering shape allowing for easier insertion thereof between cheek and teeth for example. In such a case, the suction port is turned toward the tooth while another portion of the base body, which is longer and is located opposite the suction port, rests against the cheek.

In a particularly advantageous embodiment of the invention, the inner surface of the base body is more specifically coated with a reflective coating in the region that can be viewed from the exterior. This means that the treating dentist brings the suction apparatus near the tooth in exactly the same way as usual, namely with the suction port turned toward the tooth, and may then view the tooth or the region to be treated through the suction port through the mirroring inner surface. That is, the mirror does not extend as a continuation of the suction apparatus. The advantage thereof is that the suction performance is not adversely affected since the distance to the region to be suctioned is not increased. Moreover, it has been found that the noise inevitably generated by the air draft will not increase for the same reason. This is the case with a mirror that is mounted before the suction port since said mirror may generate adverse air turbulence.

Irrespective thereof, it may be advantageous to have, instead or additionally, the outer surface of the base body coated with a reflective coating.

In another embodiment of the invention, the suction apparatus is configured with its end portion comprising the suction port being flared in order to thus raise the inner mirrored surface in particular. This makes sense if it is the inner face of the suction apparatus, which is viewable through the suction port, that is used as the reflective surface. The flared shape also allows to better keep for example soft tissue and the like out of the way.

Depending on the function desired, it may make sense if the reflective coating has a magnifying or reducing effect. Such an effect may be achieved on the one hand by the fact that the suction apparatus itself has a convex or a concave shape that is coated with a corresponding reflective or mirroring material or by the fact that a concave or a convex mirror is placed onto the base body. This mirror may be glued thereon, although it may also be formed in the material from which the base body is made. The important point is that, if an additional mirror is used, it is connected to the base body in such a manner that the suction apparatus may be readily disinfected. For this purpose, those methods may for example be used that are utilized with usual dental mirrors to connect the mirror to the retaining base body.

The use of a pluggable element comprising the mirroring surface is particularly advantageous. This element is releasably connected to the suction apparatus in the region of the suction port. The suction apparatus may for example have a groove for insertion of the pluggable element. As a result, the pluggable element may be replaced ad lib and can be adapted to desired situations. The pluggable element may have any shape, the mirroring surface can be concave, convex or of a different type.

The suction apparatus of the invention can be made of any suited material although for cost reasons it may be practical to make it from a plastic material.

In accordance with the invention, the base body is configured in such a manner that it may be caused to adapt to the desired circumstances through plastic deformation. This may for example be achieved in that the base body is made from a relatively soft, plastically deformable plastic material the treating physician will then shape as desired by simply bending it before using it in accordance with its purpose of utilization. Alternatively, the use of one or more spherical joints may also be used. The important point is that the orientation of the longitudinal axis of the suction apparatus be variable in any direction. In a particularly advantageous embodiment, such a joint is disposed near the mirroring region or the mirroring region itself is rotatable about the longitudinal axis or is configured to be pivotal with respect thereto.

Figure 2:
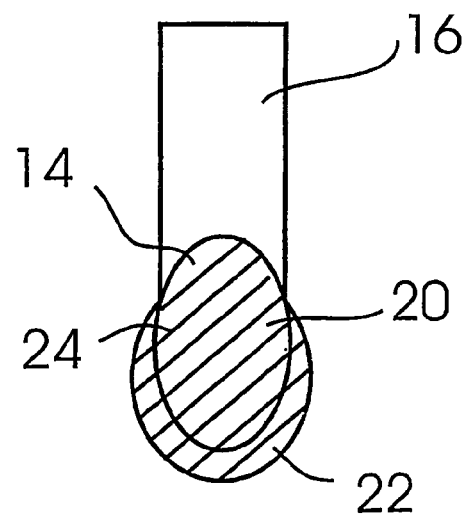
Figure 3:
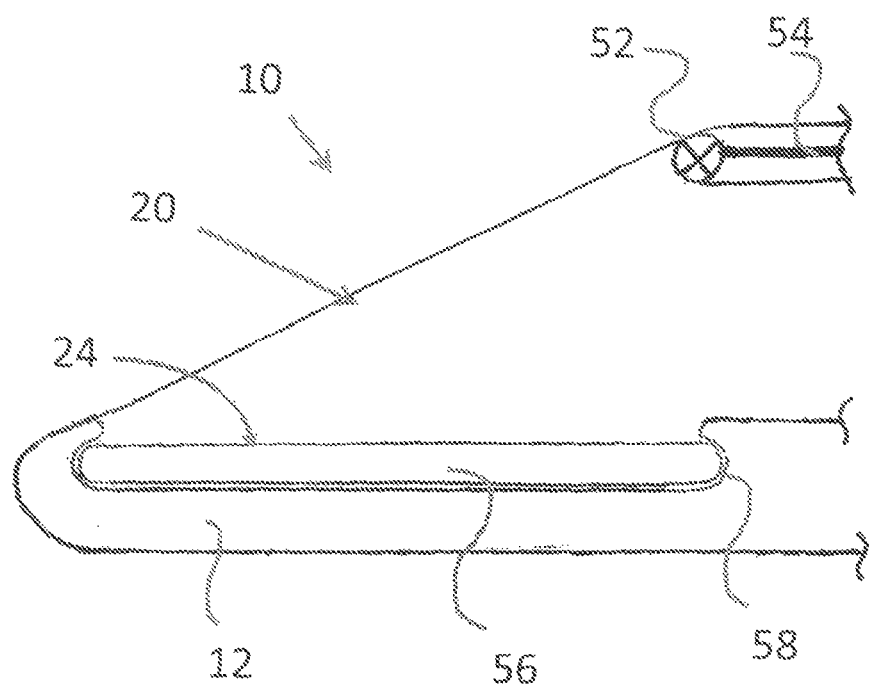

The invention will be best understood from the following description when read in conjunction with the accompanying drawings. In said drawings:

FIG. 1 shows a schematic side view illustrating a suction apparatus of the invention, FIG. 2 shows an enlarged view of that end region of the suction apparatus that has a suction port; and FIG. 3 shows a cross-sectional view of the suction apparatus with a light source and a pluggable element attached thereto.

As can be seen from the two figures, a medical suction apparatus 10 has a hollow, for example tubular, base body 12 with an inner surface 14 and an outer surface 16. The base body 12 further has a longitudinal axis X-X that may be straight or kinked, as shown in the exemplary embodiment. The kink offers the advantage that the suction apparatus 10 may be brought more easily to the treatment region.

The base body 12 has a connection port 18 and a suction port 20. The connection port 18 serves for connection to a hose that has not been illustrated herein, whereas the suction port 20 is for passage of the suctioned fluids or debris therethrough.

In the present exemplary embodiment, there is further shown a border 22 that extends about portions of the suction port 20. This border 22 is for a suction apparatus 10 utilized in dentistry to better keep the cheek or lip of the patient away from the region to be treated.

In accordance with the invention, portions of the suction apparatus 10 have a mirroring surface 24. This is shown by a hatched area. It has been found advantageous if, like in the exemplary embodiment shown, the inner surface 14 of the suction apparatus 10 is configured to be mirrored in the region that can be viewed through the suction port 20 for example. This is exactly the region that, during treatment for example, is located opposite the tooth to be treated, since it needs anyway to be brought near this region for effective cleaning. Further, thanks to the constant air draft generated by the suction at the inner surface 14 of the base body 12, it is ensured that the mirrored surface 24 will not get steamed up. Irrespective thereof however, it is possible to also provide portions of the outer surface 16 with a mirroring surface 24, as shown in FIG. 1. The border 22 may also preferably be configured to be wider as shown in order to increase the mirroring surface area.

It may also be sensible to have all the visible surfaces of the base body 12 provided with a mirroring surface 24 or to have the base body 12 made from a mirroring material.

Advantageously, the suction apparatus 10 may have a light source 52 in the region of its suction port 20, said light source illuminating the region that is to be viewed through the mirroring surface 24. This may for example be ensured by an optical fiber 54 extending along the length of the base body 12. The light source 52 may be disposed directly in the region of the connection port 18 or even externally if it irradiates into the optical fiber 54.

FIG. 3. illustrates that the mirroring surface 24 could be disposed on a pluggable element 56 that is releasably connected to the suction apparatus 10. As such, the suction apparatus 10 may include a groove 58 for insertion of the pluggable element 56 in the region of the suction port 20.

The base body 12 may be manufactured from any suited material; a hard plastic material for example is appropriate because it is easy to disinfect. In order to ensure the deformability in accordance with the invention, the base body may be made in parts of a softer material or have portions similar to a pleated bellows. A pleated bellows has the advantage that the suction apparatus 10 can be shortened or lengthened.

With the suction apparatus 10 of the invention, the treating person can treat the patient from behind (from the 12 o'clock position). This is considerably less tiring for the back of the treating person as she may now bend over the patient from the top. Since the use of suction apparatus is very current in dentistry, the invention can appreciably contribute to improved ergonomics in the workplace.

The invention is not limited to the exemplary embodiments described; it also covers all equivalent embodiments. The embodiment variant described has only been given by way of example and is not intended to limit the scope of the invention in any manner.

The invention claimed is:

1. A dental suction apparatus for suctioning fluids and debris from the mouth cavity of a patient during a treatment, said apparatus comprising a unitary passageway defined by a unitary hollow base body, said hollow base body comprising an outer surface and an inner surface, a proximal end portion and a distal end portion; said distal end portion having a bevelled tapered suction tip; a mirror is located on the inner surface of the bevelled tapered suction tip so that at least parts of the mouth can be viewed through the suction tip.

2. The dental suction apparatus as set forth in claim 1, said suction tip being configured to be at an incline with respect to a longitudinal axis X-X, that the area of the suction tip exceeds a cross-sectional area of the base body extending across the longitudinal axis.

3. The dental suction apparatus as set forth in claim 1, wherein the mirror is disposed on a pluggable element that is releasably connected to the suction apparatus.

4. The dental suction apparatus as set forth in claim 3, wherein a groove for insertion of the pluggable element is disposed in the region of the suction tip.

5. The dental suction apparatus as set forth in claim 1, wherein the base body is configured to be deformable in the longitudinal direction in such a manner that the orientation of a longitudinal axis X-X may be varied.

6. The dental suction apparatus as set forth in claim 5, wherein the base body is made from a flexible plastic material.

7. The dental suction apparatus as set forth in claim 1, wherein a light source is disposed in the region of the suction tip so as to illuminate the region to be reflected.

8. A dental suction apparatus for suctioning fluids and debris from the mouth cavity of a patient during a treatment, said apparatus having a unitary passageway defined by a unitary hollow base body, said hollow base body comprising an outer surface and an inner surface, a proximal end portion and a distal end portion; said distal end portion having a bevelled tapered suction tip, and a mirror located on the inner surface of the bevelled tapered suction tip, wherein the base body is configured to be deformable in the longitudinal direction in such a manner that the orientation of a longitudinal axis X-X may be varied.

* * * * *